United States Patent
Levina

(10) Patent No.: US 9,433,623 B2
(45) Date of Patent: Sep. 6, 2016

(54) MEDICINAL DRUG WITH ACTIVITY AGAINST GRAM POSITIVE BACTERIA, MYCOBACTERIA AND FUNGI

(76) Inventor: Elizabeth Levina, New York, NY (US)

( * ) Notice: Subject to any disclaimer, the term of this patent is extended or adjusted under 35 U.S.C. 154(b) by 0 days.

(21) Appl. No.: 14/427,915

(22) PCT Filed: Sep. 14, 2012

(86) PCT No.: PCT/US2012/055404
§ 371 (c)(1),
(2), (4) Date: Mar. 12, 2015

(87) PCT Pub. No.: WO2014/042647
PCT Pub. Date: Mar. 20, 2014

(65) Prior Publication Data
US 2016/0000786 A1    Jan. 7, 2016

(51) Int. Cl.
*A61K 31/515* (2006.01)
*A01N 43/54* (2006.01)
*A61K 31/04* (2006.01)
*A61K 31/11* (2006.01)
*A61K 31/15* (2006.01)

(52) U.S. Cl.
CPC .............. *A61K 31/515* (2013.01); *A01N 43/54* (2013.01); *A61K 31/04* (2013.01); *A61K 31/11* (2013.01); *A61K 31/15* (2013.01)

(58) Field of Classification Search
CPC .................................................. A61K 31/515
USPC ......................................................... 549/370
See application file for complete search history.

(56) References Cited

PUBLICATIONS

Surechem Electronic Database Search of Oct. 23, 2012 for Application No. PCT/US12/55404.
Pelttari et al., Antimicrobial Properties of Substituted Salicylaldehydes and Related Compounds, 2007.
Radulovic et al., Antimicrobial synergism and antagonism of salicylaldehyde in Filipndula vulgaris essential oil, May 24, 2007.
Al-Obaidi, Synthesis, Characterization and Theoretical Treatment of Sandwich Schiiff Bases Complexes Derived from Salicylaldehyde with some Transition Metals and Study of its.

*Primary Examiner* — Taofiq A Solola
(74) *Attorney, Agent, or Firm* — John D Gugliotta

(57) ABSTRACT

The invention relates to chemistry and pharmacology, in particular to synthetic biologically active substances of the pyrimidine series that have antimicrobial activity, and to the method of synthesis thereof. According to the invention there is provided a new substance with activity against gram positive bacteria, mycobacteria and fungi characterized in that it constitutes 5-(2-hydroxybenzylidene) derivatives of the pyrimidinone series with the general formula 1 where XI, X3 are selected from the group containing: H, halogen; N02; X2, X4 are selected from the group containing: H, halogen: Z is selected from the group containing: 0, NNH2, NOH, pei†iydropyrimidine-5-ytidene-2,4,6-trione, perhydropyrimidine-5-ylidene-2,4,6-trione, substituted at the nitrogen atom With alkyl, aryl or aralkyl group; Y is selected from the group containing: H, Na, Li, K.

1 Claim, 16 Drawing Sheets

MEDICINAL DRUG WITH ACTIVITY AGAINST GRAM POSITIVE BACTERIA, MYCOBACTERIA AND FUNGI

TECHNICAL FIELD

The invention relates to chemistry and pharmacology, in particular to synthetic biologically active substances obtained on the basis of perhydropyrimidine-2,4,6-triones (barbituric acids) and derivatives of salicylic aldehyde that have antimicrobial activity, and to the method of synthesis thereof. The inventive substances are products of condensation of substituted derivatives. The inventive substances are novel derivatives of salicylic aldehyde with barbituric acid, N-substituted barbituric acids, or other novel derivatives of salicylic aldehyde.

The invention applies to all stereoisomers of the claimed substances, all their tautomeric and salt forms and also adducts with some organic acids.

The substances are intended for use in medical practice for treating diseases caused by microorganisms, as well as for similar purposes in veterinary medicine. The substances can be used either individually or in the form of their pharmaceutically acceptable salts and complexes.

BACKGROUND ART

Contemporary literature shows considerable interest in derivatives of barbituric acids due to their influence on various enzyme systems [2—Novac L., Kovac B. Electronic structure and biological activity: barbiturates end thiobarbiturates//Shem. Phys. Lett. 2010, 493, 242-[244]. Of particular interest are 5-arylidene derivatives of barbituric acids that have anticonvulsant, antimicrobial, spasmolytic, antipyretic and antineoplastic activity [3—Sans R. G., Chosas M. G.//Pharmazie, 1988, Bd 43, N 12, S. 827-829]. New publications appear that study antibacterial properties of 5-arylidene barbituric acids [4]—Yan Q., Cao R., Yi W., Shen Z., Wen H., Ma L., Song H.//Inhibitory effects of 5-arylidene barbiturate derivatives on mushroom tyrozinase and their antibacterial activity//Eur. J. Med. Chem., 2009, 44, 4235-4243].

Earlier many other S-arylidene barbituric acids have been, discovered to have valuable biological properties—pesticide, antineoplastic, antimicrobial inammosuppressive, nootropic, antihypertensive and antiallergic [5]—Singh. A., Mohan R. R., Misra V. S.//Indian Drugs., 1985, Vol. 22; N 8. P. 418-422 (Chemical Abstracts, Vol. 104, 129855c).
[6]—Singh S., Gupta G. P., Shanker K.//Indian J. Chem., 1985, Vol. 24B, N 10, P, 1094-1097.
[7]—Singh A., Misra V. S.//Pharmacol. Res., 1989, Vol. 21, N 1, P. 59-64 (Chemical Abstracts, Vol. 111, 49906z).
[8]—Kumar P., Nath C., Agarwal J. C., Bhargava K. P., Shanker K.//Indian J. Chem., 1983. Vol 22B, N 9, P. 955-958.
[9]—patent of Japan, international classifier A 61K 31/505. No 05213755, pending since Feb. 7, 1992 (92/56671), published on Aug. 24, 1993 (Chemical Abstracts, 1993. Vol. 119, 262520r).
[10]—Kumar A., Singh S., Saxena A. K., Shanker K.//Indian J. Chem., Sect. 1988, Vol. 27, N 5, P. 443-447.
[11]—Hirota K., Fukazawa T., Isobe Y., Morita H., European Patent Office application No. 546661 in international classifier. S 07D 239/62, pending since Oct. 9, 1991 (91/290538), published on Jun. 16, 1993 (Chemical Abstracts, Vol. 119, 180814a).

The abovementioned references indicate that the search for a new antibacterial agents among barbituric acids, in particular among 5-arylidene derivatives of barbituric acid, has good potential.

High variability of bacteria that results in the emergence and fast propagation of antibiotic resistance among bacteria does not allow achieving significant clinical results in treatment of a large number of diseases of different localizations caused by said bacteria. Medicine needs new drugs that have no analogues and consequently do not have resistant clones circulating around. The discovered peculiarities of microbial activity in biofilms have shown the necessity of selecting antimicrobial drugs with new properties.

*Staphylococcus aureus* is arguably the most problematic pathogen faced by modern healthcare systems today, owing in large part to the persistent emergence of antibiotic resistant strains. This is perhaps most evident in the recent appearance of methicillin-resistant strains even among isolates causing community-acquired infection. Moreover, many of these strains have the capacity to cause serious, life-threatening infection even in otherwise healthy individuals. This accounts in large part for the observation that in the United States alone an estimated more than 100,000 patients suffered from invasive infection caused by Methicillin-resistant *Staphylococcus aureus* (MRSA) [http://www.ndhealth.gov/disease/Documents/Resources/MRSA%20Book/MRSAVRE.pdf], with approximately 20,000 resulting in a fatal outcome. The continued emergence of antibiotic-resistant strains has created an urgent need for new antimicrobial agents.

Ampicillin antibiotic was selected as the prototype or the current invention, since its biological effect has the greatest similarity to the to inventive agent. Ampicillins inhibit one of the enzymes involved in the synthesis of the bacterial ceil walls. The loss of the stability conferred by the wall leads to the cell lysing.

Ampicillin is represented as the following compound:

6-[[2R)-aminophenylacetyl]amino]3,3-dimethyl-7-oxo-4-thia-1 azabicyclo[3.2.0]heptane-2carboxylic acid, see: [http://pubchem.ncbi.nlm.nih.gov/summary/summary.cgi-?cid=6249].

Ampicillin is a broad spectrum antibiotic, but it has no effect on Methycillin Resistant *Staphylococcus aureus* (MRSA) mycobacteria and fungi, and has poor penetration rate into bacterial biofilms [Davies D. Understanding biofilm resistance to antibacterial agents. Nat Rev Drag Discov 2003; 2:144-122; Anderl, J. N., Franklin M. J., Stewart P. S., Role of antibiotic penetration limitation in *Klebsiella pneumoniae* biofilm resistance to ampicilin and ciprofloxacin. Animticrob. Agents Chemother. 2000. 44:1818-1824.]

SUMMARY OF THE INVENTION

It is an object of the invention to provide novel chemical compounds with increased antibacterial activity and wider range of action.

According to the invention there are provided novel antimicrobial substances that are created through synthesis and have the following general formula (1):

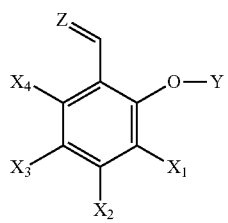

where X1, X3 are selected from the group containing: H, halogen: $NO_2$;

X2, X4 are selected from the group containing: H, halogen;

Z is selected iron; the group containing: O, $NNH_2$, NOH, perhydropyrimidine-5-ylidene-2,4,6-trione, perhydropyrimidine-5-ylidene-2,4,6-trione, substituted at the nitrogen atom with alkyl, aryl or aralkyl group;

Y is selected from the group containing: H, Na, Li, K.

The invention applies to all stereoisomers of the claimed substances, all their tautomeric and salt forms, and also adducts with some organic acids—formic acid, acetic acid, propionic acid lactic acid, benzoic acid, salicylic acid.

The applicant has not found any sources of information containing data on engineering solutions identical to this invention, which enables to conclude that the Invention conforms to the criterion "Novelty" (N).

The applicant has not found any sources of information contain am data on the influence of the features of the invention on the technical result produced by the invention. In applicant's opinion, these facts enable to conclude that the invention conforms to the criterion "Inventive Step" (IS).

BRIEF DESCRIPTION OF THE DRAWINGS

The invention is further explained, by way of detailed description of examples of its embodiments, without reference to any drawings.

PREFERRED EMBODIMENT

Figure 1:
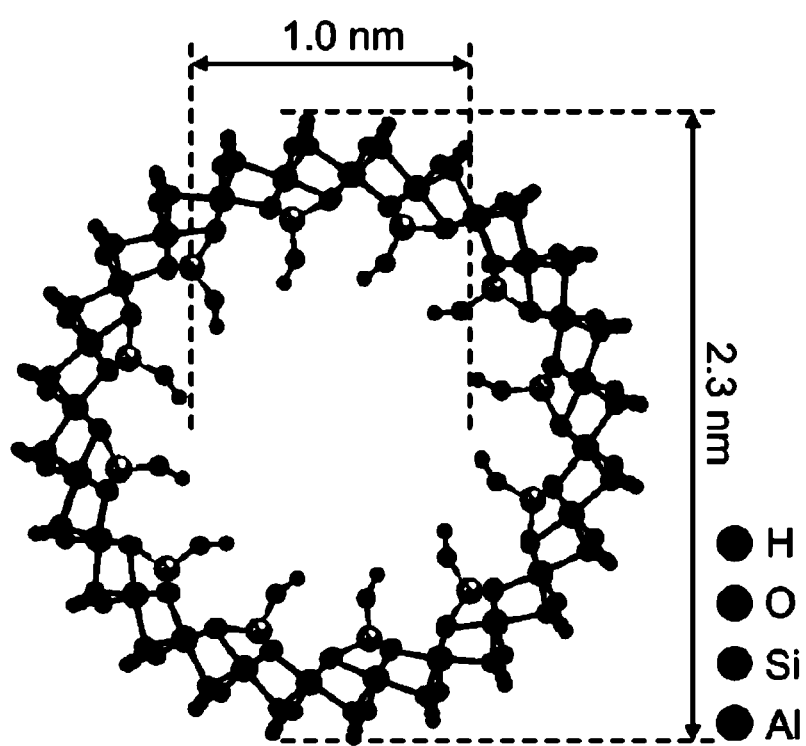
Figure 2:
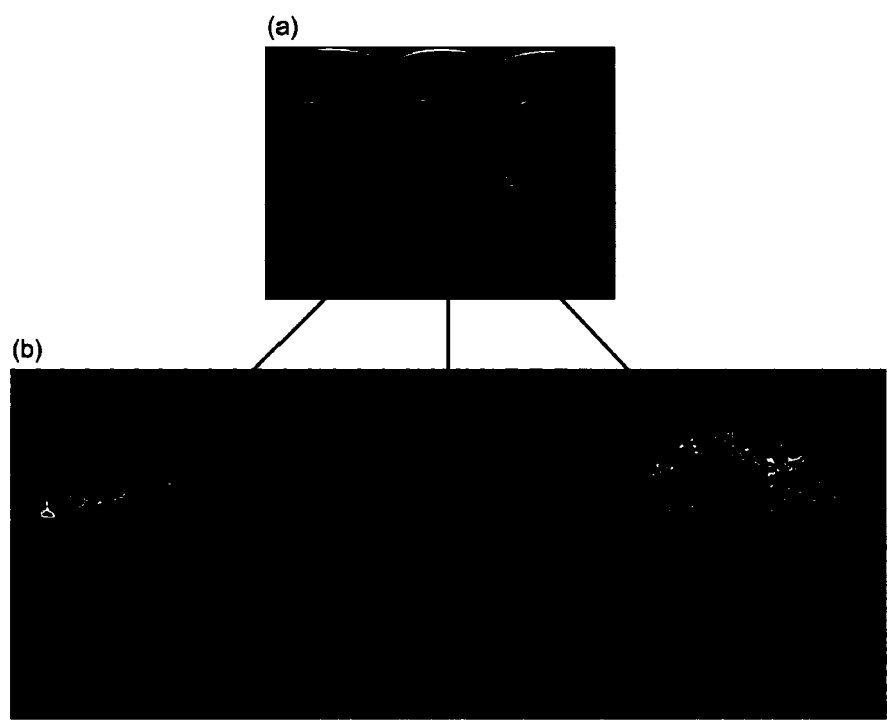
Figure 3:
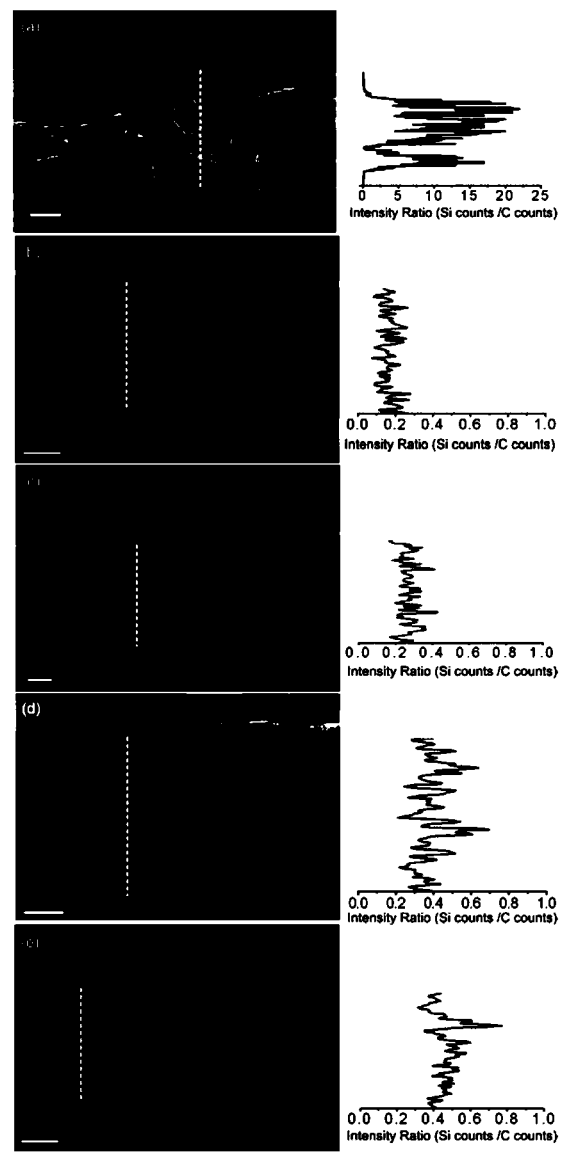
Figure 4:
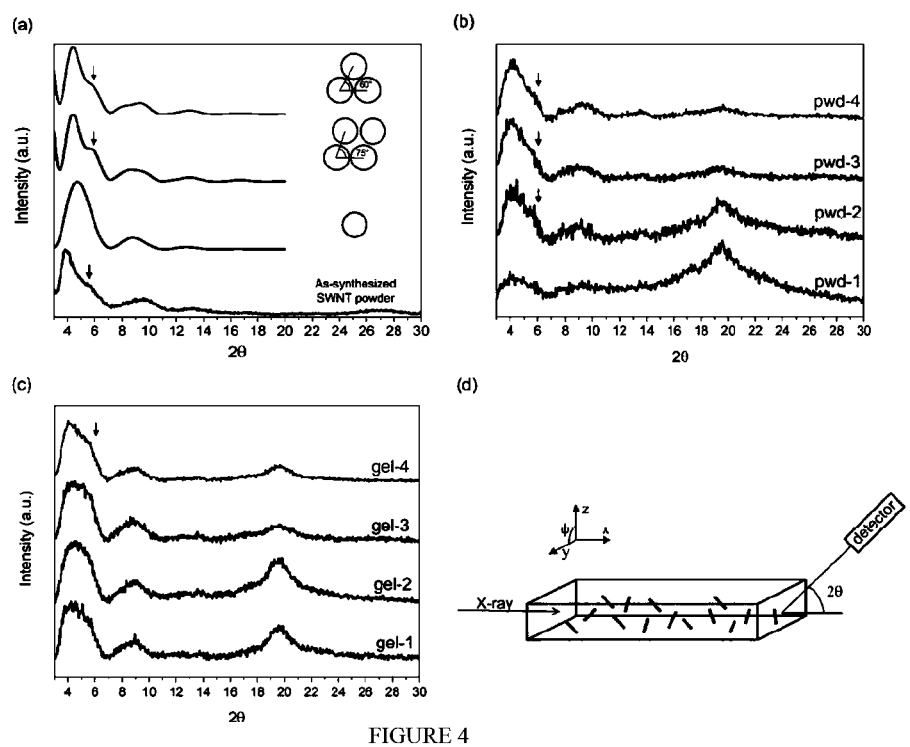
Figure 5:
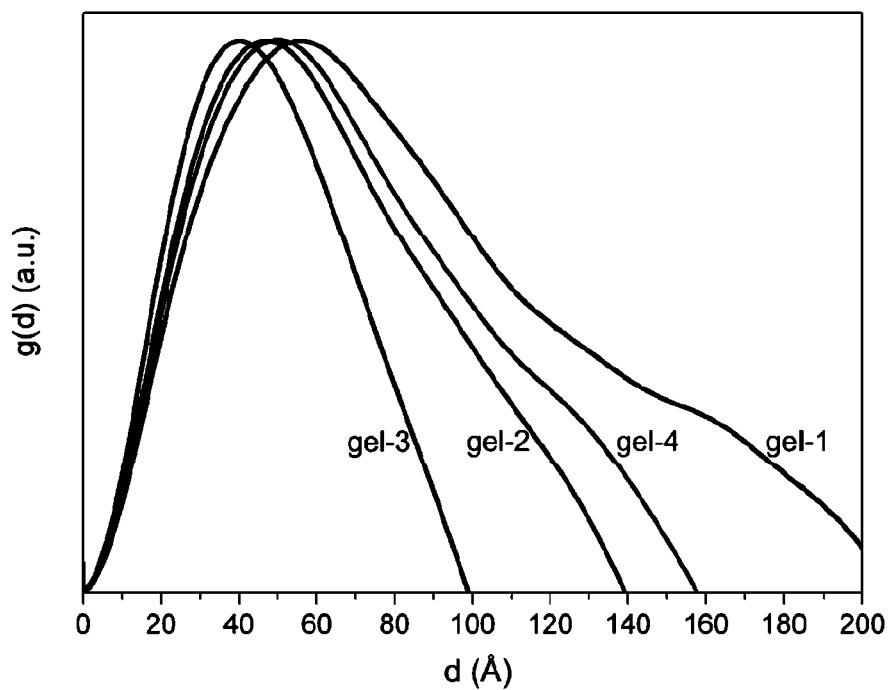
Figure 6:
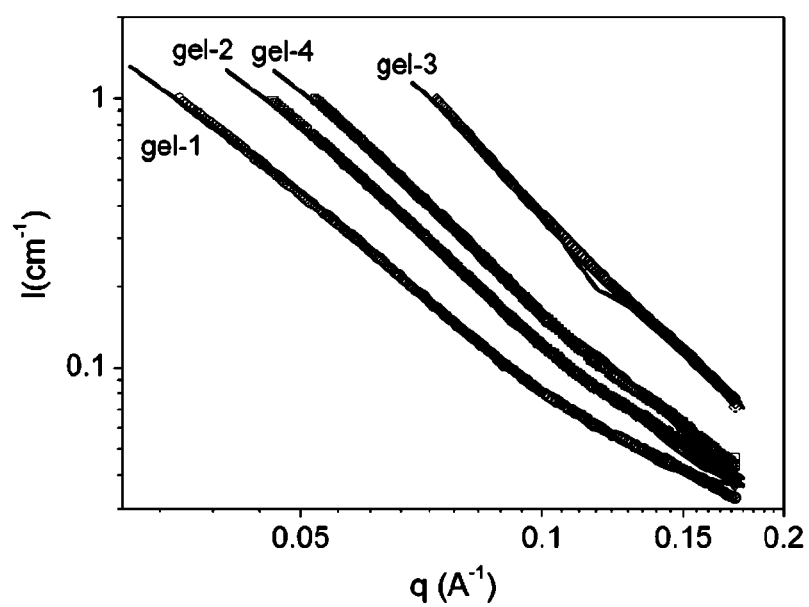
Figure 7:
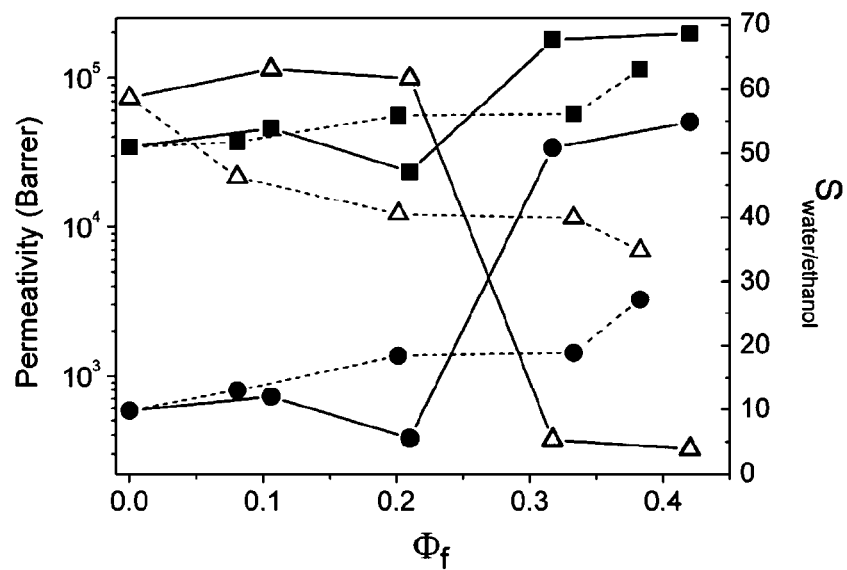
Figure 8:
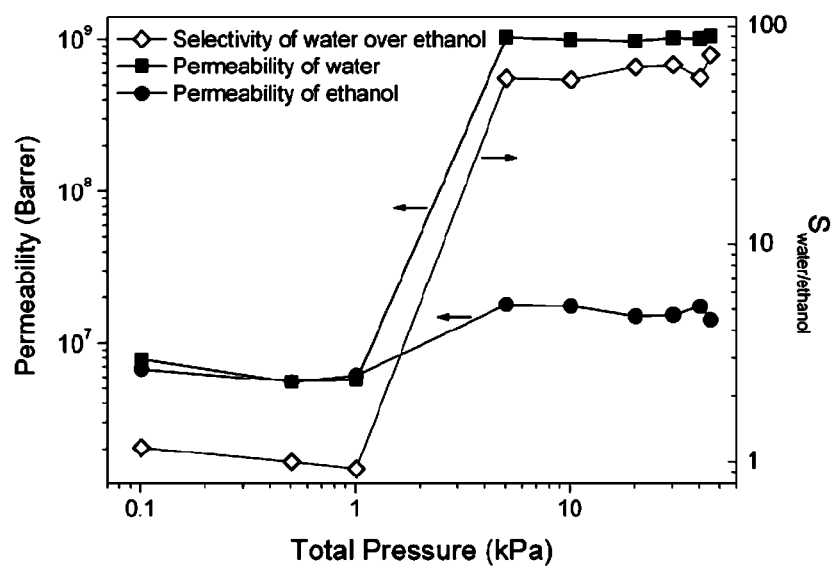
Figure 9:
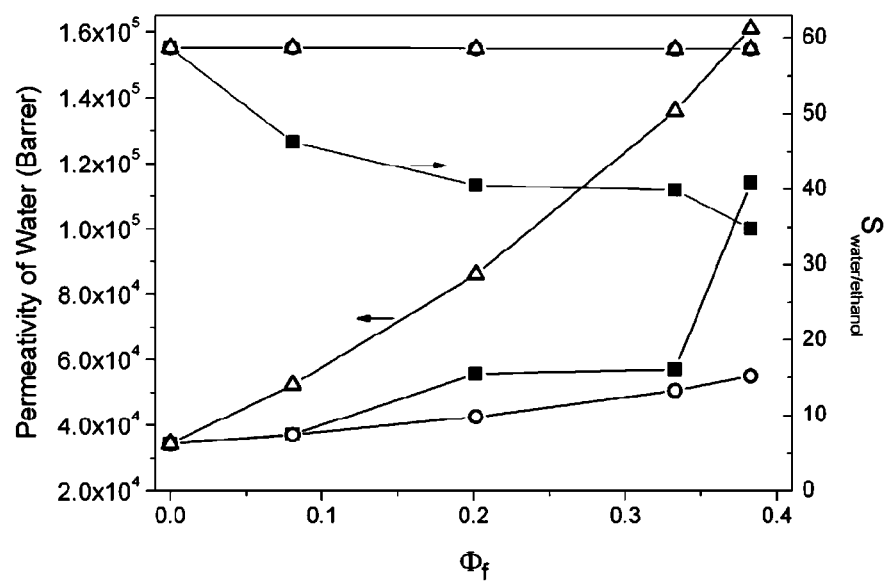
Figure 10:
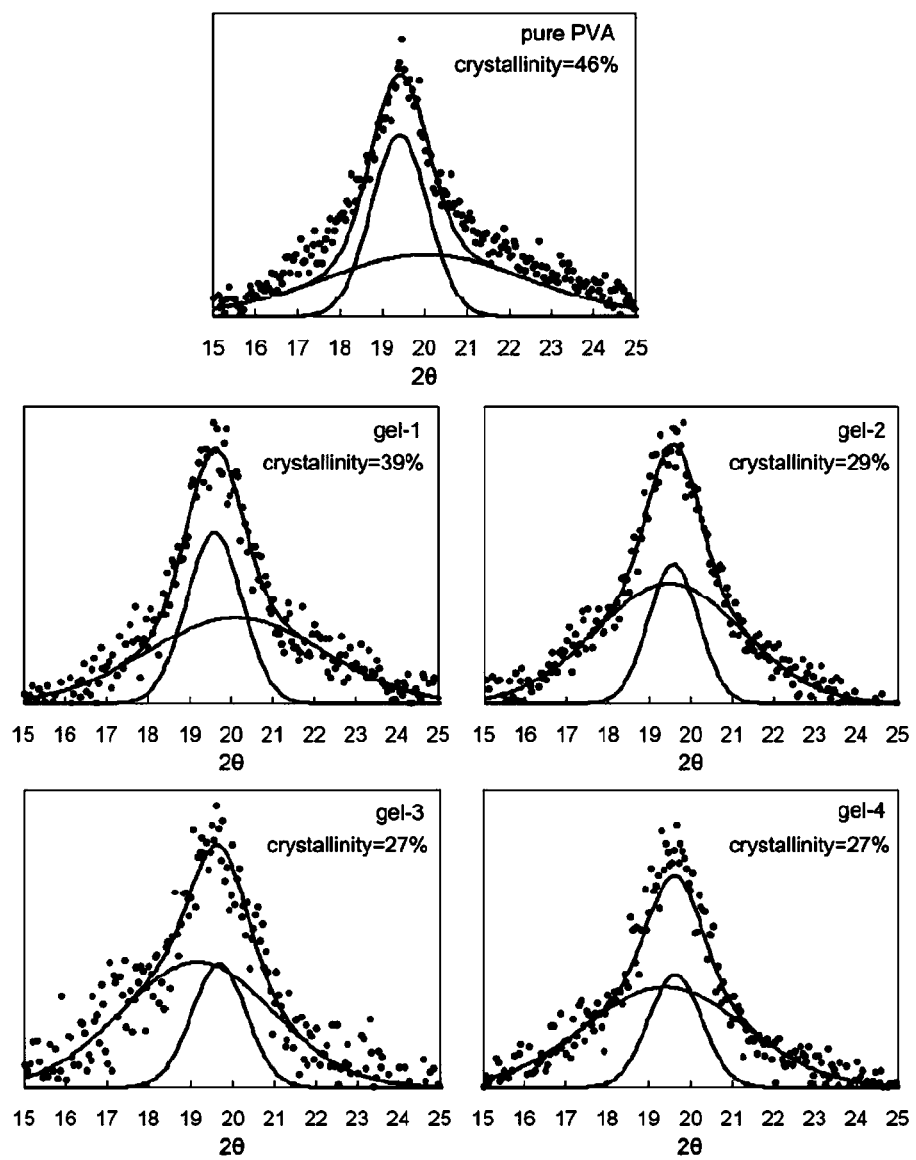
Figure 11:
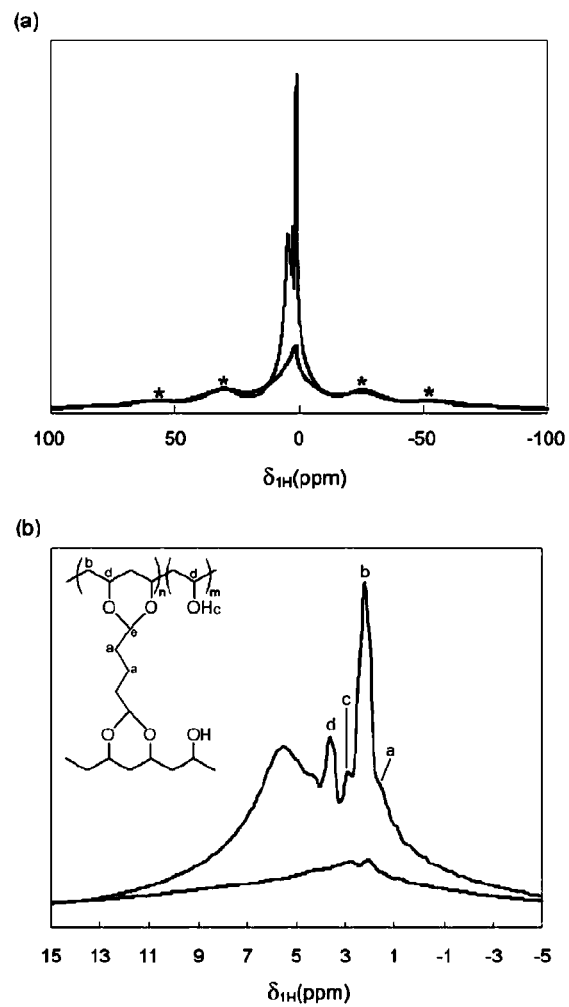
Figure 12:
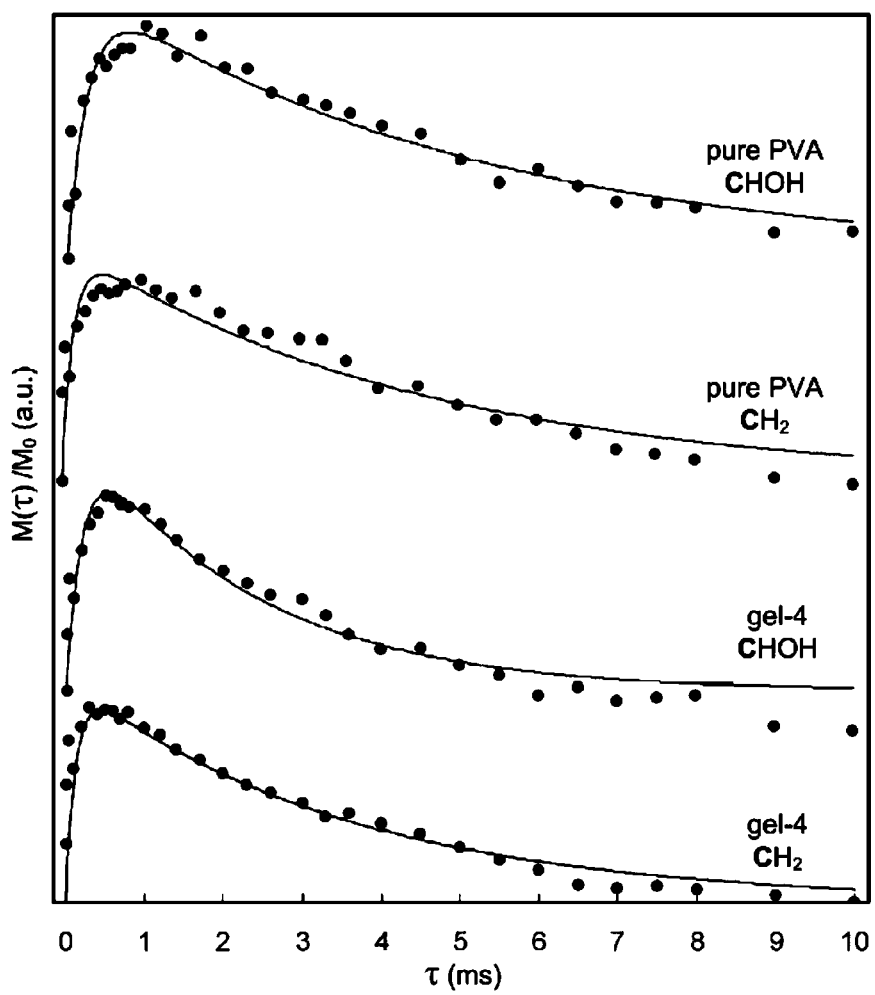
Figure 13:
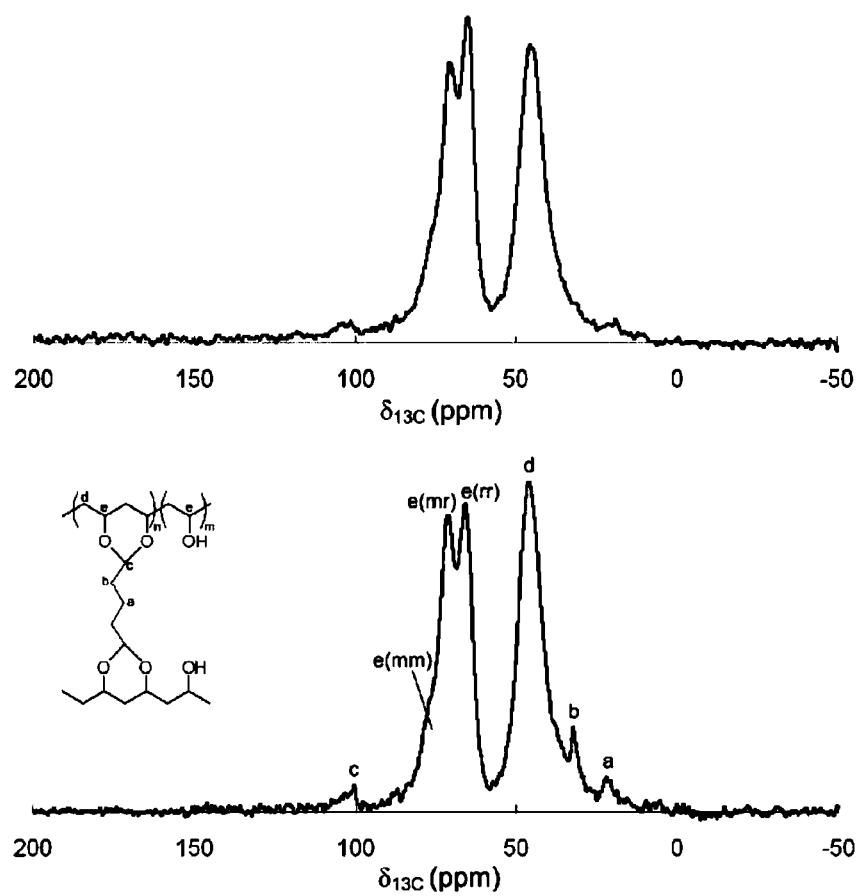
Figure 14:
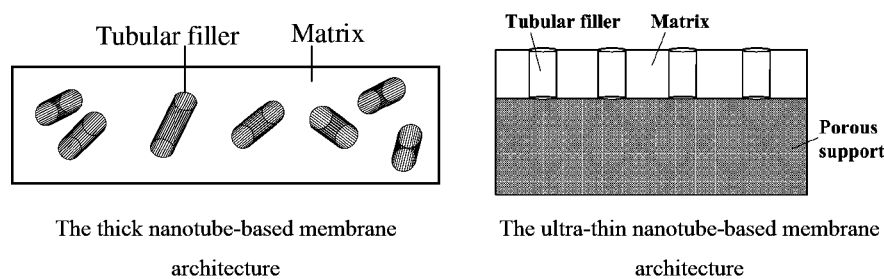
Figure 15:
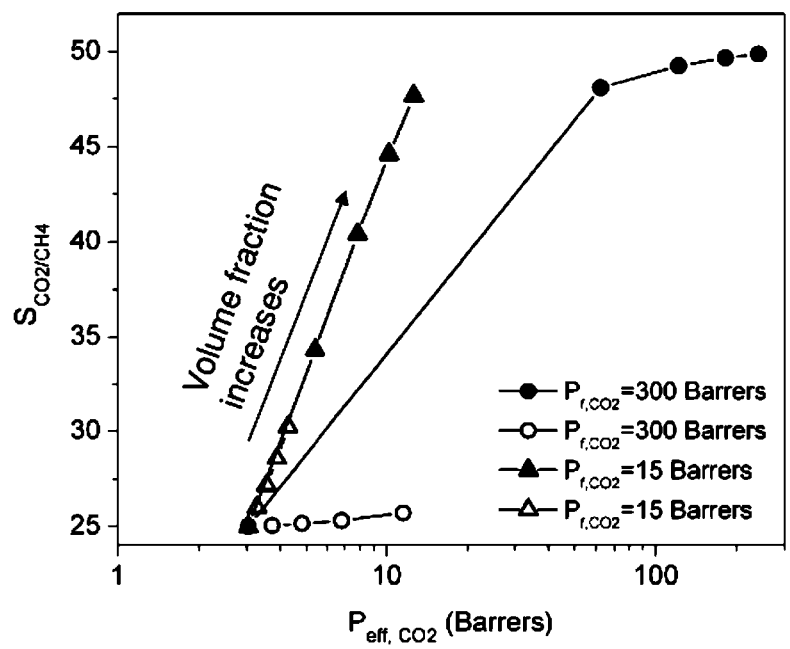
Figure 16:
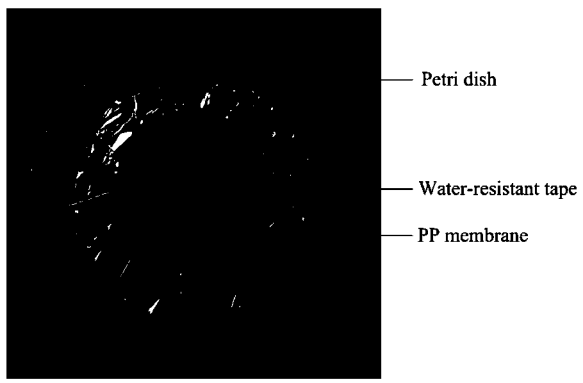
Figure 17:
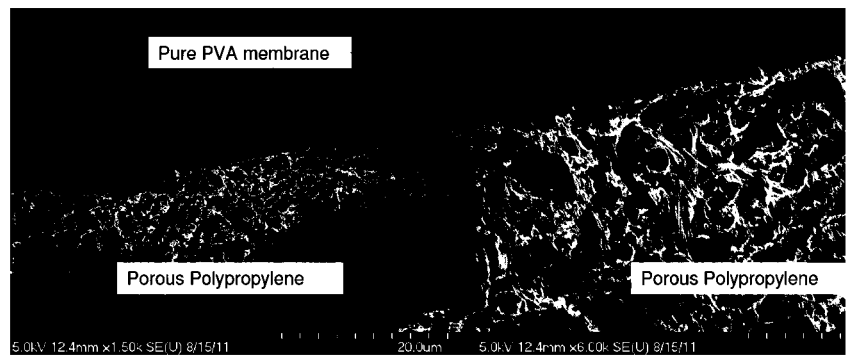
Figure 18:
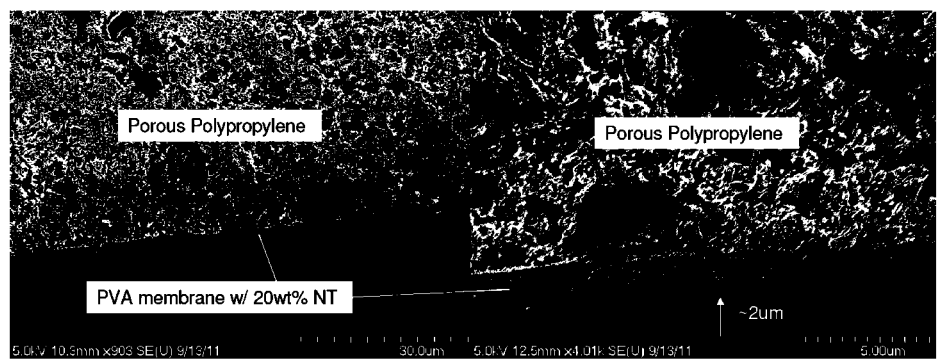

For the solution of the abovementioned problem the substances specified in table 1 are preferable.

The inventive substances 1-16 were synthesized according to procedure 1, substances 17-19—according to procedure 2, substances 20-21—according to procedure 3. Interpretation of radicals in the structure of the inventive substances is shown in Table 1.

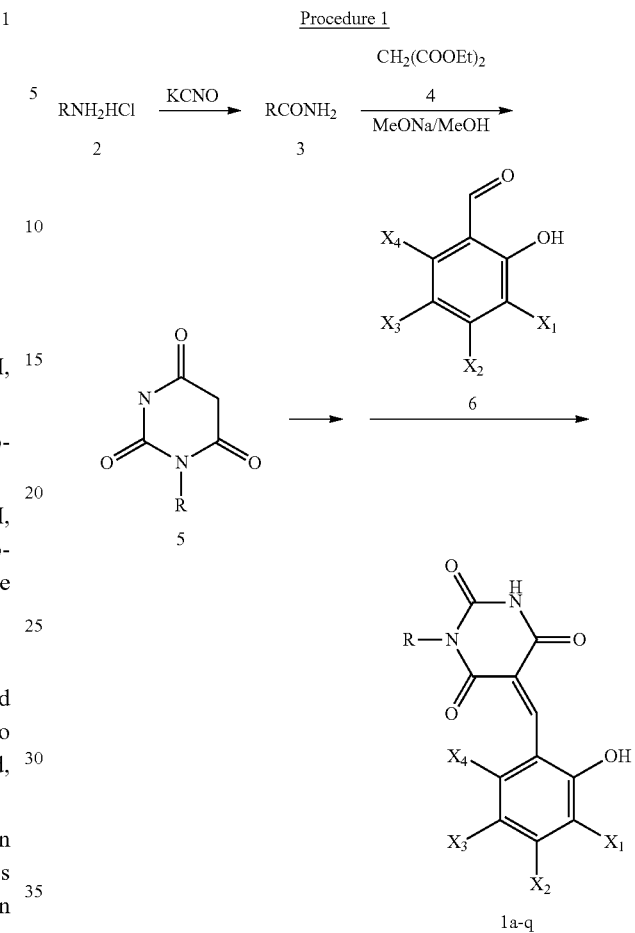

Procedure 1

5: R = H (a), $CH_3$ (b), $CH_2CH=CH_2$ (c), 4-methoxybenzyl (d), Ph (e)
6: X2 = X4 = H;
X1 = X3 = Br (a); X1 = X3 = Cl (b); X1 = X3 = H (c);
X1 = H, X3 = Br (d); X1 = H, X3 = Cl (e); X1 = H, X3 = $NO_2$ (f);
X1 = Br, X3 = $NO_2$ (g); X1 = Cl, X3 = $NO_2$ (h); X1 = X3 = I (j);
X1 = I, X3 = $NO_2$ (k); X1 = Br, X3 = I (l); X1 = I, X3 = Br (m).

Synthesis of the inventive substances: 1-16 according to procedure 1 generally comprises the following three principal stages:

1) N-alkyl urea (3) is obtained from the salt of corresponding alkylamine (2) and potassium cyanate in aqueous solution.

2) Corresponding derivative of barbituric acid 5 is obtained through cyclocondensation of N-alkyl urea 3 with diethylmalonate (4) in the presence of sodium alkoxide.

3) The inventive substance 1-16 is obtained through condensation or the derivative of barbituric acid 5 with corresponding 2-hydroxybenzaldehyde (6).

For substances 1-12 the intermediate compound (5) is implemented as barbituric acid (5a, R=H), which is an easily available chemical agent, and therefore the first two stages of the synthesis are not necessary, i.e. the substances 1-12 are synthesized in a single stage.

The inventive substances 17-19 are obtained according to procedure 2 through treatment of corresponding derivative of 2-hydroxybenzaldehyde (6) with aqueous-alcoholic solution of YOH alkali, where Y—Li, Na or K.

Procedure 2

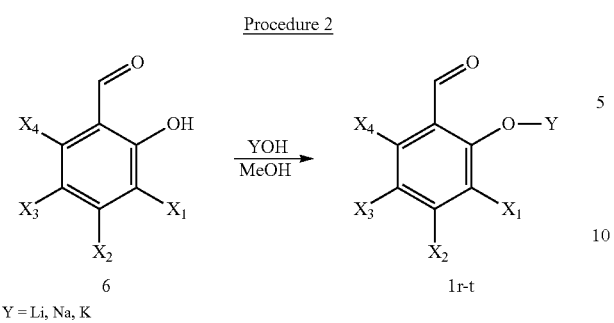

Y = Li, Na, K

The inventive substances 20, 21 are obtained according to procedure 3 through treatment of corresponding derivative of 2-hydroxybenzaldehyde (6) with hydrazine-hydrate or hydroxylamine in an alcoholic solution with subsequent treatment by means of alcoholic solution of YOH alkali, where Y—Li, Na or K.

Procedure 3

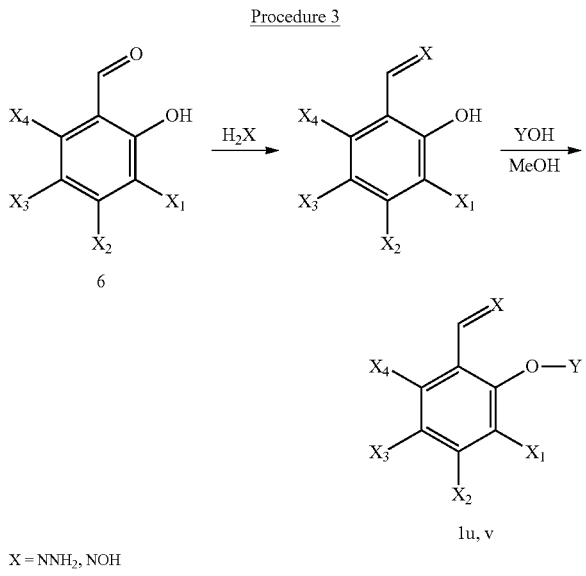

X = $NNH_2$, NOH
Y = Li, Na, K

The described method is same for all members of the group.

The essence of the invention is further explained by means of the examples of synthesis of intermediate substances, examples of synthesis of the inventive substance, tables with the output data and other characteristics of the target substances, experiments that study the biological properties of the inventive substances and tables with results of said experiments, where:
  example 1 is a specific example of the synthesis of the inventive substance (obtaining target substances 1-12);
  example 2 is a specific example of the synthesis of the inventive substance (obtaining target substances 13-16);
  example 3 is a specific example of the synthesis of the inventive substance (obtaining target substances 17-19);
  example 4 is a specific example of the synthesis of the inventive substance (obtaining target substances 20-21);
  experiment 1 evaluates the antibacterial activity;
  experiment 2 evaluates the antibacterial activity of the inventive substances against resistant bacterial strains;
  experiment 3 evaluates the acute toxicity;
  table 1 describes the structure of the inventive derivatives (1-21);
  table 2 shows the data of $^1H$ NMR spectra of the target substances (1-21);
  table 3 shows the data of elemental analysis of the target substances (1-21).

EXAMPLE 1

Alternative embodiment of synthesis of the inventive substance—obtaining 5-(3,5-dibromo-2-hydroxybenzylidene) perhydropyrimidine-2,4,6-trione (1a)

0.01 mol (1.28 g) of barbituric acid (5a) were dissolved in 25 ml of glacial acetic acid while heating. Then 0.011 mol (3.08 g) of 3,5-dibromo-2-hydroxybenzaldehyde (6a) were added to the obtained solution while stirring and the resulting reaction mixture was left at room temperature during 36 hours. The produced crystal product was filtered, washed with cold acetic acid, then washed with ether and air-dried. Thereby 3.3 g of product 1a were obtained in the form of yellow needle crystals with melting temperature of 255-260° C. (with decomposition). Output amounted to 77% of the theoretical value.

Similar procedure was used to obtain the following from barbituric acid (5a) and corresponding aldehyde (6):
  5-(3,5-dichloro-2-hydroxybenzylidene) perhydropyrimidine-2,4,6-trione (2), melting temperature 260-263° C. (with decomposition), the output amounted to 71% of the theoretical value;
  5-(5-bromo-2-hydroxybenzylidene) perhydropyrimidene-2,4,6-trione (3), melting temperature 256-258° C. (with decomposition), the output amounted to 74% of the theoretical value;
  5-(5-chloro-2-hydroxybenzylidene) perhydropyrimidine-2,4,6-trione (4), melting temperature 260-263° C. (with decomposition), the output amounted to 75% of the theoretical value;
  5-(5-nitro-2-hydroxybenzylidene) perhydropyrimidine-2,4,6-trione (5), melting temperature 240-245° C. (with decomposition), the output amounted to 70% of the theoretical value;
  5-(3-bromo-5-nitro-2-hydroxybenzylidene) perhydropyrimidine-2,4,6-trione (7), melting temperature 241-243° C. (with decomposition), the output amounted to 66% of the theoretical value;
  5-(3-chloro-5-nitro-2-hydroxybenzylidene) perhydropyrimidine-2,4,6-trione (8), melting temperature 241-245° C. (with decomposition), the output amounted to 69% of the theoretical value;
  5-(3,5-diiodo-2-hydroxybenzylidene) perhydropyrimidine-2,4,6-trione (9), melting temperature 251-265° C. (with decomposition), the output amounted, to 79% of the theoretical value;
  5-(3-iodo-5-nitro-2-hydroxybenzylidene) perhydropyrimidine-2,4,6-trione (1k) (10), melting temperature 233-236° C. (with decomposition), the output amounted to 61% of the theoretical value;
  5-(3-bromo-5-iodo-2-hydroxybenzylidene) perhydropyrimidine-2,4,6-trione (11), melting temperature 255-259° C. (with decomposition), the output amounted to 68% of the theoretical value;

5-(3-iodo-5-bromo-2-hydroxybenzylidene) perhydropyrimidine-2,4,6-trione, melting temperature 260-264° C. (with decomposition), the output amounted to 70% of the theoretical value.

EXAMPLE 2

Alternative embodiment of synthesis of the inventive substance—obtaining 1-methyl-5-(3,5-dibromo-2-hydroxybenzylidene) perhydropyrimidine-2,4,6-trione (13) (procedure 1)

2.1. 1-methyl urea (3a), 0.1 mol (6.7 g) of methylamine hydrochloride (2) were dissolved in 30 ml of water while heating to 50° C. A solution of 0.11 mol (8.1 g) of potassium cyanate in 35 ml of water was poured to the obtained solution while stirring, the resulting mixture was heated for 15 minutes and then stripped to dryness at a water bath, the residue was extracted with isopropanol and the obtained extract was stripped to dryness in vacuum until obtaining constant weight. 6.2 g of product 3a with melting temperature 89° C. were obtained. Output amounted to 88% of the theoretical, value.

2.2. 1-methyl barbituric avid (5b), 0.2 mol (4.6 g) of sodium metal were dissolved in 60 ml of anhydrous methanol. 0.1 mol (16 g) of diethyl malonic ether (4) were added to the obtained solution and stirred for 5 minutes. Then 0.1 mol (7.2 g) of N-methyl urea (3b R=$CH_3$) were added and the resulting mixture was boiled for 3 hours under reflux while stirring. Then ⅔ of methanol were distilled, the mixture was corned down to 25° C. and 25 ml of water were added. The solution was acidified with HCl to pH 1 and sustained at 10° C., the precipitated residue was filtered, washed with cold water and dried. 11.5 g of 1-methyl barbituric acid 5b with melting temperature 142-143° S were obtained. Output amounted to 83% of the theoretical value.

2,3,1-methyl-5-(3,5-dibromo-2-hydroxybenzylidene)perhydropyrimidine-2,4,6-trione (13)

The inventive substance 9 with melting temperature 202-205° S was obtained from 1-methyl barbituric acid 5b and 3,5-dibromo-2-hydroxybenzaldehyde (6a) according to a technique similar to the technique described in Example 1, the output amounted to 74% of the theoretical value.

Substituted barbituric acids 5b-d were obtained according to a technique similar to the technique described in example 2, in accordance with Procedure 1, and were condensed with 3,5-dibromo-2-hydroxybenzaldehyde (6a) to obtain the following:

1-allyl-5-(3,5-dibromo-2-hydroxybenzylidene) perhydroyrimidine-2,4,6-trione (14), melting temperature 206-210° C. the output amounted to 69% of the theoretical value;

1-(4-methoxybenzyl-5-(3,5-dibromo-2-hydroxybenzylidene) perhydroyrimidine-2,4,6-trione (15), melting temperature 205-207° C. the output amounted to 66% of the theoretical value;

1-phenyl-5-(3,5-dibromo-2-hydroxybenzylidene) perhydroyrimidine-2,4,6-trione (16), melting temperature 226-229° C., the output amounted to 70% of the theoretical value.

EXAMPLE 3

Alternative embodiment of synthesis of the inventive substance—obtaining 2-formyl-4,6-dibromo sodium phenolate (17), (procedure 2)

Aqueous methanol solution of 0.01 mol (0.4 g) of caustic soda was added to methanol solution of 0.01 mol (2.80 g) of 3,5-dibromo-2-hydroxybenzaldehyde (5a) and the resulting reaction mixture was led at room temperature. The produced crystal product was filtered, washed with methanol, then washed with ether and air-dried, 2.9 g of product 17 were obtained in the form of yellow microcrystalline powder with melting temperature of 260-262° C. (with decomposition). Output amounted to 90% of the theoretical value.

The following was obtained from 3,5-dibromo-2-hydroxybenzaldehyde (5a) and lithium hydroxide according to a technique similar to that of Example 3:

2-formyl-4,6-dibromo lithium phenolate (18), melting temperature 259-260° C. the output amounted to 85% of the theoretical value.

The following was obtained from 3-bromo-5-nitro-2-hydroxybenzaldehyde (5@@g) and potassium hydroxide according to a technique similar to that of Example 3:

2-formyl-4-bromo-6-nitro potassium phenolate (19) melting temperature 272-273° C., the output amounted to 88% of the theoretical value.

EXAMPLE 4

Alternative embodiment of synthesis of the inventive substance—obtaining hydrazone of 2-formyl-4,6-dibromo sodium phenolate (20).

0.01 mol (0.5 g) of hydrazine-hydrate were added to methanol solution of 0.01 mol (2.80 g) of 3,5-dibromo-2-hydroxybenzaldehyde (5a) stirred for 20 minutes and then 0.01 mol (0.4 g) methanol solution of caustic soda were poured into the produced solution. The obtained reaction mixture was left at room temperature, the produced crystal product was filtered, washed with methanol, then washed with ether and air-dried. 2.56 g of product 20 were obtained in the form of yellow crystals with melting temperature of 260-262° C. (with decomposition). Output amounted to 81% of the theoretical value.

The following was obtained from 3,5-dibromo-2-hydroxybenzaldehyde (5a), hydroxylamine and potassium hydroxide according to a technique similar to that of Example 3:

oxime of 2-formyl-4,6-dibromo sodium phenolate (21), melting temperature 250° C. (decomp.), the output amounted to 72% of the theoretical value.

Bacterial Assay: Determination of Antibacterial Activity, Compounds of the invention were tested for antimicrobial activity by susceptibility testing in liquid, or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. Methods for Dilution Antimicrobial Susceptibility Tests for Bacteria That Grow Aerobically; Approved Standard-Seventh Edition. Document M7-A7. CLSI, Wayne, Pa., 2006; Clinical Laboratories and Standards Institute.

Experiment 2

The gram positive bacterial strains tested include *Staphylococcus aureus* ATCC 29213, *S. aureas* MRSA 24/31, *S. aureus* MRSA 201/010. *Enterococcus faecalis* is ATCC 29212, *Streptococcus pyogenes* ATCC 51339. The gram negative bacterial strains tested include *Haemophilus influenza* ATCC 49247. *Mycobacteria—Mycobacteria tuberculosis* H37Rv, Fungi: *Candida albicans* ATCC 10231, *Aspergillus fumigatus* ATCC 204305

MICs where of #, 15, 17, and 19. 15 were up to: 1.5-3.1 mg/l for *S. aureus* ATCC 29213, *S. aureas* MRSA 24/31, *S. aureus* MRSA 201/010; 0.7-1.5 mg/l for *E. faecalis* ATCC 29212, *S. pyogenes* ATCC 51339; 6.5-12.5 for *M. tuberculosis* H3Rv; 3.1-6.2 for *C. albicans* ATCC 10231 and *A. fumigatus* ATCC 204305/

In the same conditions the reference agent (ampicillin) had no effect on all strains of fungi and MRSA that were used.

Experiment 3

Control platings of cultures to solid culture media showed no growth, which indicates that the substances have bactericidal action.

The best activity was observed for compound #1, 15, 17, 19. The inventive substances penetrate and kill bacteria and fungi within biofilms. Biofilms used in testing were produced by 24-hour cultivation in 96-well plates.

Alter 24-hour action of the compound #1 upon biofilms of *S. aureus* ATCC 29213, *S. aureus* MRSA 24/31. *S. aureus* MRSA 201/010, the number of CFU decreased by 10,000 times, whereas the effect of 10 mg/l of ampicillin on *S. aureus* ATCC 29213 reduced the number of CFU by 10 times only, and for MRSA strains said substance had no effect whatsoever.

INDUSTRIAL APPLICABILITY

The invention can be implemented by means of known materials and equipment. In applicant's opinion, this enables to conclude that the inventions conform to the criterion "Industrial Applicability" (IA).

Structure of the Most Active Inventive Derivatives (1a-x) with the General Formula 1

TABLE 1

| № | X1 | X2 | X3 | X4 | Y | Z |
|---|----|----|----|----|---|---|
| 1 | Br | H | Br | H | H | (structure) |
| 2 | Sl | H | Cl | H | H | (structure) |
| 3 | H | H | H | H | H | (structure) |
| 4 | H | H | Br | H | H | (structure) |
| 5 | H | H | Cl | H | H | (structure) |
| 6 | H | H | $NO_2$ | H | H | (structure) |
| 7 | Br | H | $NO_2$ | H | H | (structure) |
| 8 | Cl | H | $NO_2$ | H | H | (structure) |
| 9 | I | H | I | H | H | (structure) |
| 10 | I | H | $NO_2$ | H | H | (structure) |
| 11 | Br | H | I | H | H | (structure) |

TABLE 1-continued

| № | X1 | X2 | X3 | X4 | Y | Z |
|---|----|----|----|----|---|---|
| 12 | I | H | Br | H | H | (5-substituted barbituric acid, NH, NH) |
| 13 | Br | H | Br | H | H | (5-substituted barbituric acid, N-CH$_3$) |
| 14 | Br | H | Br | H | H | (5-substituted barbituric acid, N-allyl) |
| 15 | Br | H | Br | H | H | (5-substituted barbituric acid, N-CH$_2$-C$_6$H$_4$-OMe) |
| 16 | Br | H | Br | H | H | (5-substituted barbituric acid, N-phenyl) |
| 17 | Br | H | Br | H | Na | O |
| 18 | Br | H | Br | H | Li | O |
| 19 | Br | H | NO$_2$ | H | K | O |
| 20 | Br | H | Br | H | Na | N—NH$_2$ |
| 21 | Br | H | Br | H | K | N—OH |

Data of $^1$H NMR Spectra of the Target Substances
DMSO-d$_6$

TABLE 2

| No. of the substance | ArH | SH=, s, 1H | OH, bel. s, 1H | NH, s, 1H | Other H |
|---|---|---|---|---|---|
| 1 | 7.76 d (1H), 7.91 d (1H) | 8.26 | 10.34 | 11.21, 11.39 | — |
| 2 | 7.64 d (1H), 7.77 d (1H) | 8.27 | 10.32 | 11.28, 11.44 | — |
| 3 | 6.90 m (1H), 7.24 m (1H), 7.64 m (1H), 7.77 m (1H) | 8.29 | 10.15 | 11.29, 11.47 | — |
| 4 | 7.05 m (1H), 7.18 m (1H), 7.31 d (1H), | 8.32 | 10.40 | 11.22, 11.38 | — |
| 5 | 7.12 m (1H), 7.33 m (1H), 7.50 d (1H), | 8.27 | 10.38 | 11.20, 11.42 | — |
| 6 | 7.70 m (1H), 7.92 m (1H), 8.08 d (1H), | 8.28 | 10.46 | 11.19, 11.36 | — |
| 7 | 8.09 s (1H), 8.14 s (1H) | 8.26 | 10.45 | 11.20, 11.36 | — |
| 8 | 7.86 d (1H), 8.11 d (1H) | 8.26 | 10.48 | 11.25, 11.43 | — |
| 9 | 7.59 s (1H), 7.70 s (1H) | 8.31 | 10.40 | 11.24, 11.40 | — |
| 10 | 7.81 s (1H), 8.10 s (1H) | 8.30 | 10.46 | 11.20, 11.38 | — |
| 11 | 7.70 s (1H), 7.82 s (1H) | 8.29 | 10.43 | 11.22, 11.39 | — |
| 12 | 7.66 s (1H), 7.79 s (1H) | 8.33 | 10.40 | 11.23, 11.41 | — |
| 13 | 7.78 d (1H), 7.93 d (1H) | 8.38 | 10.41 | 11.55 + 11.72 (0.5H + 0.5H)* | 3.51 |
| 14 | 7.78 d (1H), 7.92 d (1H) | 8.40 | 10.44 | 11.51 + 11.64 (0.5H + 0.5H)* | 4.01 m (2H, NCH$_2$), 5.56 m (2H, =CH$_2$), 5.90m(2H, =CH) |
| 15 | 6.85 (2H), 7.27 (2H), 7.28 (1H), 7.85 + 7.92 (1H)* | 8.32 + 8.36* (0.5H + 0.5H) | 10.36 | 11.54 + 11.71 (0.5H + 0.5H)* | 3.73 + 3.75 s + s (1.5H + 1.5H, OMe), 4.87 + 4.92 s + s (1H + 1H, NSH$_2$)* |
| 16 | 7.28-7.65 m (7H) | 8.30 + 8.33* (0.5H + 0.5H) | 10.35 | 11.72 + 11.85 (0.5H + 0.5H)* | — |
| 17 | 7.81 d (1H), 7.94 d (1H) | 9.70 | — | — | — |
| 18 | 7.80 d (1H), 7.92 d (1H) | 9.66 | — | — | — |
| 19 | 8.55 d (1H), 8.82 d (1H) | 9.96 | — | — | — |
| 20 | 7.44 d (1H), 7.99 d (1H) | 7.80 | — | 5.50 ppm (2H) | — |
| 21 | 7.60 d (1H), 7.87 d (1H) | 8.05 | 10.22 | — | — |

*NOTE.
The double set of signals in $^1$H NMR spectrum is caused by the presence of Z- and E- isomers Data of Elemental Analysis of the Target Substances

TABLE 3

| No. of the substance | Found, % | | | | Calculated, % | | |
|---|---|---|---|---|---|---|---|
| | S | H | N | Gross formula | S | H | N |
| 1 | 33.76 | 1.59 | 7.11 | $S_{11}H_6Br_2N_2O_4$ | 33.88 | 1.55 | 7.18 |
| 2 | 43.70 | 2.05 | 8.98 | $S_{11}H_6Cl_2N_2O_4$ | 43.88 | 2.01 | 9.03 |
| 3 | 56.74 | 3.53 | 11.99 | $S_{11}H_8N_2O_4$ | 56.90 | 3.47 | 12.06 |
| 4 | 42.35 | 2.32 | 8.91 | $S_{11}H_7BrN_2O_4$ | 42.47 | 2.27 | 9.00 |
| 5 | 49.50 | 2.69 | 10.44 | $S_{11}H_7ClN_2O_4$ | 49.55 | 2.65 | 10.51 |
| 6 | 47.57 | 2.58 | 15.13 | $S_{11}H_7N_3O_6$ | 47.66 | 2.55 | 15.16 |
| 7 | 37.04 | 1.74 | 11.71 | $S_{11}H_6BrN_3O_6$ | 37.10 | 1.70 | 11.80 |
| 8 | 42.28 | 1.98 | 13.40 | $S_{11}H_6ClN_3O_6$ | 42.40 | 1.94 | 13.48 |
| 9 | 27.37 | 1.29 | 5.71 | $S_{11}H_6I_2N_2O_4$ | 27.30 | 1.25 | 5.79 |
| 10 | 32.66 | 1.54 | 10.31 | $S_{11}H_6IN_3O_6$ | 32.78 | 1.50 | 10.42 |
| 11 | 30.10 | 1.42 | 6.33 | $S_{11}H_6BrIN_2O_4$ | 30.23 | 1.38 | 6.41 |
| 12 | 30.14 | 1.41 | 6.36 | $S_{11}H_6BrIN_2O_4$ | 30.23 | 1.38 | 6.41 |
| 13 | 35.75 | 2.04 | 6.88 | $S_{12}H_8Br_2N_2O_4$ | 35.68 | 2.00 | 6.93 |
| 14 | 39.19 | 2.30 | 6.46 | $S_{14}H_{10}Br_2N_2O_4$ | 39.10 | 2.34 | 6.51 |
| 15 | 44.77 | 2.78 | 5.44 | $S_{19}H_{14}Br_2N_2O_5$ | 44.73 | 2.77 | 5.49 |
| 16 | 43.87 | 2.19 | 5.93 | $S_{17}H_{19}Br_2N_2O_4$ | 43.81 | 2.16 | 6.01 |
| 17 | 27.64 | 1.02 | — | $S_7H_3Br_2NaO_2$ | 27.85 | 1.00 | — |
| 18 | 29.22 | 1.09 | — | $S_7H_3Br_2LiO_2$ | 29.41 | 1.06 | — |
| 19 | 29.41 | 1.09 | 4.88 | $S_7H_3Br_2KNO_4$ | 29.59 | 1.06 | 4.93 |
| 20 | 26.39 | 1.64 | 8.80 | $S_7H_5Br_2N_2NaO$ | 26.61 | 1.60 | 8.87 |
| 21 | 25.11 | 1.25 | 4.12 | $S_7H_4Br_2KNO_2$ | 25.25 | 1.21 | 4.21 |

The invention claimed is:

1. Medicinal drug with activity against gram positive bacteria, mycobacteria and fungi characterized in that it is a compound of the class of pyrimidine derivatives of salicylic aldehyde and perhydropyrimidine-2,4,6-triones with the general formula:

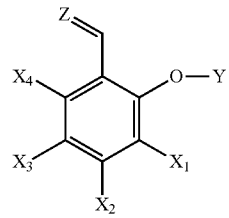

1 where $X_1$, $X_3$ are selected from the group containing: H, halogen; $NO_2$;

$X_2$, $X_4$ are selected from the group containing: H, halogen;

Z is selected from the group containing: O, $NNH_2$, NOH, perhydropyrimidine-5-ylidene-2,4,6-trione, perhydropyrimidine-5-ylidene-2,4,6-trione, substituted at the nitrogen atom with alkyl, aryl or aralkyl group;

Y is selected from the group containing: H, Na, Li, K.

* * * * *